(12) United States Patent
Keshwani

(10) Patent No.: US 12,106,856 B2
(45) Date of Patent: Oct. 1, 2024

(54) IMAGE PROCESSING APPARATUS, IMAGE PROCESSING METHOD, AND PROGRAM FOR SEGMENTATION CORRECTION OF MEDICAL IMAGE

(71) Applicant: FUJIFILM Corporation, Tokyo (JP)

(72) Inventor: Deepak Keshwani, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 578 days.

(21) Appl. No.: 17/326,349

(22) Filed: May 21, 2021

(65) Prior Publication Data

US 2021/0271914 A1 Sep. 2, 2021

Related U.S. Application Data

(63) Continuation of application No. PCT/JP2019/044867, filed on Nov. 15, 2019.

(30) Foreign Application Priority Data

Nov. 30, 2018 (JP) .................................. 2018-225019

(51) Int. Cl.
*G06T 7/11* (2017.01)
*G06F 18/21* (2023.01)
(Continued)

(52) U.S. Cl.
CPC ........... *G16H 50/20* (2018.01); *G06F 18/214* (2023.01); *G06F 18/2163* (2023.01);
(Continued)

(58) Field of Classification Search
None
See application file for complete search history.

(56) References Cited

U.S. PATENT DOCUMENTS 5,830,141 A 11/1998 Makram-Ebeid et al.
10,109,052 B2 10/2018 Chefd'hotel et al.
(Continued)

FOREIGN PATENT DOCUMENTS

JP H09134434 5/1997
JP 2015097127 5/2015
(Continued)

OTHER PUBLICATIONS

"Table (database)—Wikipedia" Published on Dec. 30, 2016 https://web.archive.org/web/20161230192449/https://en.wikipedia.org/wiki/Table_(database).*
(Continued)

*Primary Examiner* — Rinna Yi
(74) *Attorney, Agent, or Firm* — JCIPRNET

(57) ABSTRACT

Provided are an image processing apparatus, an image processing method, and a program that can reduce the time and effort required to correct the segmentation of a medical image. An image processing apparatus includes: an image acquisition unit (40) that acquires a medical image (200); a segmentation unit (42) that performs segmentation on the medical image acquired by the image acquisition unit and classifies the medical image into prescribed classes for each local region; a global feature acquisition unit (46) that acquires a global feature indicating an overall feature of the medical image; and a correction unit (44) that corrects a class of a correction target region that is a local region whose class is to be corrected in the medical image according to the global feature with reference to a relationship between the global feature and the class.

10 Claims, 10 Drawing Sheets

(51) Int. Cl.

| | |
|---|---|
| *G06F 18/214* | (2023.01) |
| *G06F 18/2431* | (2023.01) |
| *G06N 20/00* | (2019.01) |
| *G06V 10/25* | (2022.01) |
| *G06V 10/764* | (2022.01) |
| *G06V 10/82* | (2022.01) |
| *G16H 30/40* | (2018.01) |
| *G16H 50/20* | (2018.01) |

(52) U.S. Cl.
CPC ......... *G06F 18/2431* (2023.01); *G06N 20/00* (2019.01); *G06T 7/11* (2017.01); *G06V 10/25* (2022.01); *G06V 10/764* (2022.01); *G06V 10/82* (2022.01); *G16H 30/40* (2018.01); *G06T 2207/20081* (2013.01); *G06T 2207/20084* (2013.01); *G06T 2207/30061* (2013.01); *G06T 2207/30096* (2013.01); *G06V 2201/03* (2022.01)

(56) References Cited

U.S. PATENT DOCUMENTS

| | | | |
|---|---|---|---|
| 10,140,544 B1 | 11/2018 | Zhao et al. | |
| 10,366,785 B2 | 7/2019 | Wakasugi et al. | |
| 10,529,072 B2 | 1/2020 | Chefd'hotel et al. | |
| 10,706,542 B2 | 7/2020 | Chefd'hotel et al. | |
| 10,984,907 B2 | 4/2021 | Wakasugi et al. | |
| 2008/0267471 A1* | 10/2008 | Yu | G06T 7/0012 |
| | | | 382/128 |
| 2012/0082368 A1* | 4/2012 | Hirai | H04N 13/128 |
| | | | 382/154 |
| 2015/0310638 A1* | 10/2015 | Jia | G16H 50/30 |
| | | | 382/131 |
| 2016/0335478 A1* | 11/2016 | Bredno | A61B 34/74 |
| 2017/0132450 A1 | 5/2017 | El-Zehiry et al. | |
| 2018/0144182 A1 | 5/2018 | El-Zehiry et al. | |
| 2018/0239951 A1 | 8/2018 | El-Zehiry et al. | |
| 2019/0087638 A1 | 3/2019 | El-Zehiry et al. | |
| 2020/0286233 A1 | 9/2020 | Chefd'Hotel et al. | |
| 2020/0286614 A1* | 9/2020 | Do | G06N 7/01 |
| 2020/0315455 A1* | 10/2020 | Lee | A61B 5/4082 |
| 2022/0019860 A1* | 1/2022 | Weese | G06N 20/00 |

FOREIGN PATENT DOCUMENTS

| | | |
|---|---|---|
| JP | 2017516992 | 6/2017 |
| JP | 2017519985 | 7/2017 |
| JP | 2018061771 | 4/2018 |
| JP | 2018102916 | 7/2018 |

OTHER PUBLICATIONS

"International Search Report (Form PCT/ISA/210) of PCT/JP2019/044867," mailed on Jan. 28, 2020, with English translation thereof, pp. 1-7.

"Written Opinion of the International Searching Authority (Form PCT/ISA/237) of PCT/JP2019/044867," mailed on Jan. 28, 2020, with English translation thereof, pp. 1-11.

Huang, Y. H. et al., "Error correction for dense semantic image labeling", arXiv: 1712.03812, Dec. 2017, pp. 1-14.

Satoshi Iizuka et al., "Let there be color!: joint end-to-end learning of global and local image priors for automatic image colorization with simultaneous classification" ACM Transactions on Graphics(TOG), vol. 35, No. 4, Jul. 2016, pp. 1-11.

* cited by examiner

FIG. 5

| CLASS / LOCAL REGION | FIRST REGION | SECOND REGION | THIRD REGION | FOURTH REGION |
|---|---|---|---|---|
| Emphysema | 0.02 | 0.22 | 0.07 | 0.01 |
| Honeycomb | 0.72 | 0.60 | 0.75 | 0.65 |
| Bronchi | 0.05 | 0.03 | 0.13 | 0.04 |
| Reticular | 0.21 | 0.15 | 0.05 | 0.30 |

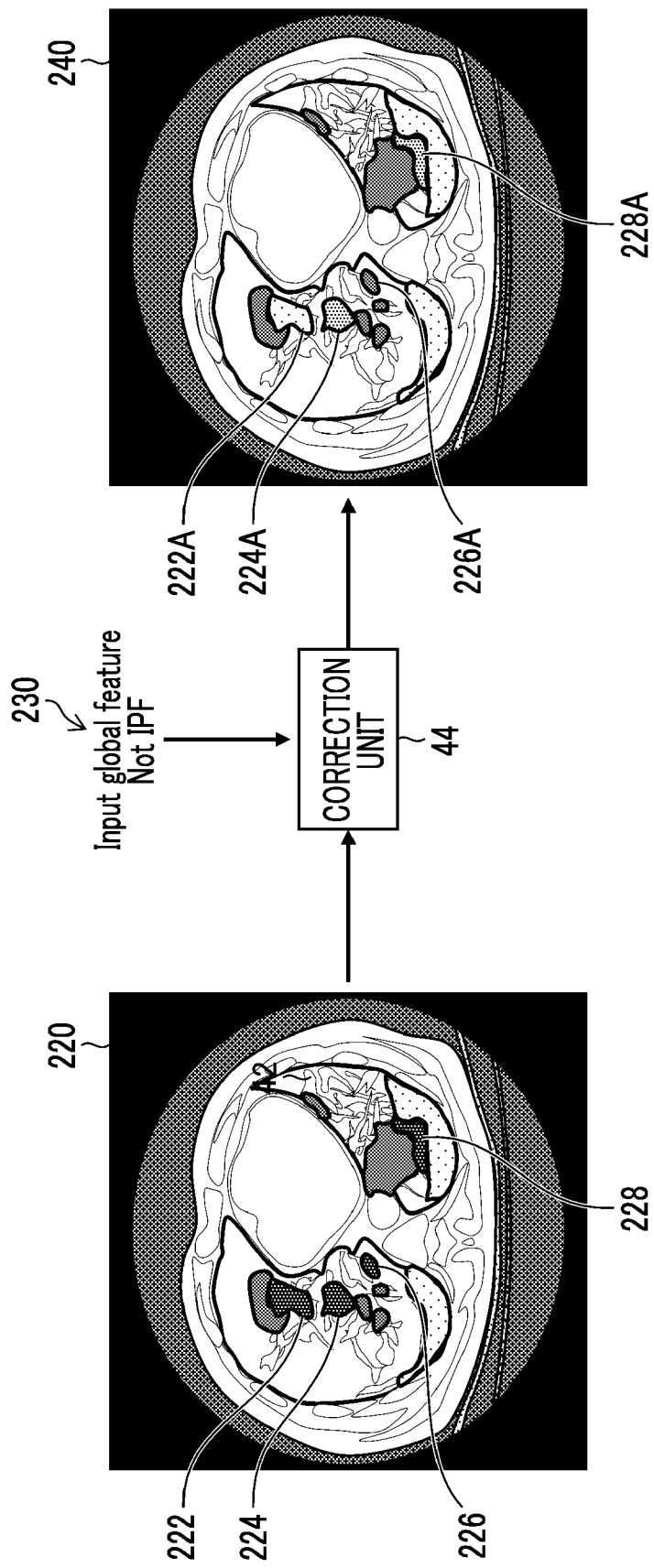

| DISEASE NAME (GLOBAL FEATURE) | LESION (CLASS) THAT CAN EXIST |
|---|---|
| COLLAGEN DISEASE LUNG ① RA | tree-in-bud appearance, BRONCHIECTASIS, TRACTION BRONCHIECTASIS, GROUND-GLASS OPACITY, HONEYCOMB LUNG |
| COLLAGEN DISEASE LUNG ② SSc (PSS) | BRONCHIECTASIS, TRACTION BRONCHIECTASIS, GROUND-GLASS OPACITY |
| CRYPTOGENIC ORGANIZING PNEUMONIA COP/OP | CONSOLIDATION, AIR BRONCHOGRAM, TRACTION BRONCHIECTASIS, GROUND-GLASS OPACITY |
| CRYPTOGENIC ORGANIZING PNEUMONIA UPPER LOBE PREDOMINANT PULMONARY FIBROSIS (PLEUROPARENCHYMAL FIBROELASTOSIS) | CONSOLIDATION, AIR BRONCHOGRAM, TRACTION BRONCHIECTASIS, GROUND-GLASS OPACITY, INTERLOBULAR SEPTAL THICKENING |
| SARCOIDOSIS: ONLY LUNG FIELD LESION | NODULAR SHADOW, GROUND-GLASS OPACITY, INTERLOBULAR SEPTAL THICKENING, BRONCHOVASCULAR BUNDLE |
| unclassifiable INTERSTITIAL PNEUMONIA | TRACTION BRONCHIECTASIS, GROUND-GLASS OPACITY, INTERLOBULAR SEPTAL THICKENING, HONEYCOMB LUNG |
| IPF ACUTE EXACERBATION | TRACTION BRONCHIECTASIS, GROUND-GLASS OPACITY, INTERLOBULAR SEPTAL THICKENING, HONEYCOMB LUNG |
| HYPERSENSITIVITY PNEUMONITIS ① SUMMER TYPE | GROUND-GLASS OPACITY, CENTRILOBULAR, MAP-LIKE |
| HYPERSENSITIVITY PNEUMONITIS ② BIRD-RELATED (INCLUDING CHRONIC TYPE) | GROUND-GLASS OPACITY, CENTRILOBULAR, MAP-LIKE |
| DIP / DIP | GROUND-GLASS OPACITY |
| CHRONIC NECROTIZING PULMONARY ASPERGILLOSIS (CNPA) | CONSOLIDATION, CAVITY, AIR BRONCHOGRAM, BRONCHIECTASIS |
| NON-TUBERCULOUS MYCOBACTERIOSIS ② *M. intracellulare* | CONSOLIDATION, CAVITY, BRONCHIAL WALL THICKENING, BRONCHIECTASIS |
| PSEUDOMONAS PNEUMONIA | CONSOLIDATION, CAVITY, BRONCHIECTASIS, tree-in-bud appearance |
| PULMONARY MUCORMYCOSIS | CONSOLIDATION, CAVITY, BRONCHIECTASIS |
| IPF / UIP | TRACTION BRONCHIECTASIS, GROUND-GLASS OPACITY, INTERLOBULAR SEPTAL THICKENING, HONEYCOMB LUNG |

IMAGE PROCESSING APPARATUS, IMAGE PROCESSING METHOD, AND PROGRAM FOR SEGMENTATION CORRECTION OF MEDICAL IMAGE

CROSS-REFERENCE TO RELATED APPLICATIONS

The present application is a Continuation of PCT International Application No. PCT/JP2019/044867 filed on Nov. 15, 2019 claiming priority under 35 U.S.C § 119(a) to Japanese Patent Application No. 2018-225019 filed on Nov. 30, 2018. Each of the above applications is hereby expressly incorporated by reference, in its entirety, into the present application.

BACKGROUND OF THE INVENTION

1. Field of the Invention

The present invention relates to an image processing apparatus, an image processing method, and a program, and more particularly, to segmentation of a medical image.

2. Description of the Related Art

The segmentation of a medical image based on anatomical features using deep learning is known. The segmentation of the medical image is used in, for example, a computer-aided diagnostic apparatus that automatically detects lesions and the like from the medical images. The use of the deep learning makes it possible to segment a complicated medical image.

JP2015-097127A discloses a diagnosis support apparatus that corrects a diagnosis result on the basis of medical knowledge data and an input operation of a user. In the apparatus disclosed in JP2015-097127A, in a case in which a finding of the doctor and a lesion name acquired by a lesion candidate acquisition unit are different from each other, the correction candidates of the diagnosis result are displayed in response to the operation of a mouse, and a message asking whether or not to adopt the correction candidates is displayed. A corrected diagnosis result is displayed in response to an operation indicating that the correction candidates are adopted.

JP2018-102916A discloses a control method that automatically identifies a lesion portion from a CT image of the lung and corrects the identification result in response to an input operation of a user. The method disclosed in JP2018-102916A selects a small region in a medical image, in which a candidate region and a correction region are superimposed and displayed on a designated target image, on the basis of the instructional information of the user.

In the method disclosed in JP2018-102916A, in a case in which it is determined that the small region is in the candidate region, pixels included in the small region are excluded from the candidate region. On the other hand, in a case in which it is determined that the small region is not in the candidate region, the pixels included in the small region are added to the candidate region. In this way, the candidate region is corrected according to the user's operation of selecting the small region, and a lesion region is finally determined.

JP2018-061771A discloses an image processing apparatus that can adjust an image feature amount extraction process for a suspected lesion region in response to the input of the user. The apparatus disclosed in JP2018-061771A performs learning for classifying an image feature label related to a suspected lesion region image and extracts the image feature amount of the suspected lesion region image using learning parameters of the image feature label obtained as the result of the learning.

Further, JP2018-061771A discloses a technique that updates the learning parameters of the image feature label in response to an input from a user input unit.

JP2017-516992A discloses an automated immune cell detection system that supports the investigation of clinical immune profiles. JP2017-516992A discloses a user interface that is used by an operator to label, for example, cells.

SUMMARY OF THE INVENTION

However, the segmentation of the medical image to which deep learning is applied may be inaccurate due to the nature of deep learning in which tasks are complex. In a case in which there is an error in the segmentation of the medical image, correction needs to be performed. On the other hand, it takes a lot of time and effort for a doctor to correct the error in the segmentation of the medical image for each pixel. Therefore, a method for efficiently correcting the segmentation is required.

The apparatus disclosed in JP2015-097127A outputs, for example, a mark designating the lesion candidate on medical examination data and an image feature amount that is the basis of the detection result as data related to the lesion candidate. That is, JP2015-097127A does not disclose a technique that outputs the segmentation result of the medical image.

Further, JP2015-097127A discloses a technique that displays the correction candidates of the diagnosis result in response to the operation of the mouse by the doctor in a case in which the finding of the doctor and the lesion name obtained by the lesion candidate acquisition unit are different from each other. However, JP2015-097127A does not disclose the correction of the segmentation of the medical image.

JP2018-102916A does not disclose the segmentation of the medical image. In addition, in the method disclosed in JP2018-102916A, the user needs to click and select the correction region in a case in which the candidate region is corrected. Therefore, it takes a lot of time and effort for the user to perform the operation.

JP2018-061771A discloses a technique that updates the learning parameters of the image feature label in response to the input from the user input unit, but does not disclose the correction of the image feature label. That is, JP2018-061771A does not disclose the correction of the segmentation of the medical image.

JP2017-516992A discloses the user interface that is used by the operator to label, for example, cells, but does not disclose the correction of the segmentation of the medical image.

The invention has been made in view of the above-mentioned problems, and an object of the invention is to provide an image processing apparatus, an image processing method, and a program that can reduce the time and effort required to correct the segmentation of a medical image.

In order to achieve the object, the invention provides the following aspects.

According to a first aspect, there is provided an image processing apparatus comprising: an image acquisition unit that acquires a medical image; a segmentation unit that performs segmentation on the medical image acquired by the image acquisition unit and classifies the medical image into classes indicating features of each local region; a global feature acquisition unit that acquires a global feature indicating an overall feature of the medical image; and a correction unit that corrects a class of a correction target region that is a local region whose class is to be corrected in the medical image according to the global feature with reference to a relationship between the global feature and the class.

According to the first aspect, the correction target region is specified according to the global feature with reference to the relationship between the global feature indicating the overall feature of the medical image and the class indicating the local feature of the medical image, and the class of the correction target region is corrected. Therefore, the correction of the class according to the global feature is automated, and it is possible to reduce the time and effort required to correct the segmentation.

The segmentation unit can generate the classification map obtained by extracting a local feature from the medical image and performing classification for each local feature.

The local region or the local portion may include an aspect composed of one pixel. Each local region or each local portion may include the concept of each pixel.

A disease name is given as an example of the global feature. The disease name may include the concept of, for example, an illness name, a disorder name, and a diagnosis name.

A lesion is given as an example of the class. The lesion may include the concept of, for example, a finding and a lesion pattern.

According to a second aspect, the image processing apparatus according to the first aspect may comprise a score calculation unit that calculates a score indicating a likelihood of each of a plurality of classes corresponding to the global feature for each local region. The segmentation unit may apply a class having a highest score as the class of each local region.

According to the second aspect, the class having the highest score indicating the likelihood of a class is adopted as the class of each local region. This makes it possible to perform segmentation based on the score and to improve the accuracy of the segmentation of the medical image.

According to a third aspect, in the image processing apparatus according to the second aspect, the correction unit may apply the class having the highest score among the classes corresponding to the global feature as the class of the correction target region in a case in which the class of the correction target region is corrected.

According to the third aspect, the correction target region is corrected to the class having the highest score among the classes corresponding to the global features. Therefore, the accuracy of the correction of the class is improved.

According to a fourth aspect, in the image processing apparatus according to the second aspect or the third aspect, the score calculation unit may calculate a probability indicating the likelihood of a class as the score.

According to the fourth aspect, it is possible to correct the class using the probability indicating the likelihood of a class.

According to a fifth aspect, in the image processing apparatus according to the first aspect or the second aspect, the correction unit may correct the class of the correction target region to a class of a local region which is at a minimum distance from the correction target region, the class of the local region being different from the class of the correction target region.

In many cases, a local region recognized as a correct class is present in the vicinity of the local region in the wrong class. According to the fifth aspect, the class of the local region at the minimum distance from the correction target region can be applied as the class of the correction target region. Therefore, it is possible to achieve at least one of shortening the period of a class correction process or reducing a processing load.

According to a sixth aspect, in the image processing apparatus according to any one of the first to fifth aspects, in a case in which the global feature acquisition unit acquires a negative global feature, the correction unit may set, as the correction target region, a local region in a class corresponding only to the global feature.

According to the sixth aspect, it is possible to correct the class which corresponds to a main portion, such as a disease name, in the global feature and is not capable of being existing in the segmentation result.

A global feature in which a term denying a feature, such as "not", is added to a main portion and which indicates the meaning of denying the main portion is given as an example of the negative global feature.

According to a seventh aspect, in the image processing apparatus according to any one of the first to fifth aspects, in a case in which the global feature acquisition unit acquires a positive global feature, the correction unit may set, as the correction target region, a local region in a class that does not correspond to the global feature.

According to the seventh aspect, it is possible to correct the class which does not correspond to the global feature and is not capable of existing in the segmentation result.

According to an eighth aspect, in the image processing apparatus according to any one of the first to seventh aspects, the correction unit may correct the class of the correction target region according to a plurality of the global features.

According to the eighth aspect, the class of the correction target region is corrected according to the plurality of global features. Therefore, the accuracy of the correction of the class can be improved.

The class of the correction target region may be corrected according to the logical product of the plurality of global features, or the class of the correction target region may be corrected according to the logical sum of the plurality of global features.

According to a ninth aspect, in the image processing apparatus according to any one of the first to eighth aspects, the correction unit may refer to a table in which the relationship between the global feature and the class is stored.

According to the ninth aspect, it is possible to correct the class with reference to the table in which the relationship between the global feature and the class of each local region is stored.

According to a tenth aspect, in the image processing apparatus according to any one of the first to ninth aspects, a machine learning device may be applied as the segmentation unit. The machine learning device may perform relearning using a set of a medical image in which a segmentation result has been corrected and a correction result of the class as learning data.

According to the tenth aspect, the performance of the segmentation unit can be improved.

According to an eleventh aspect, there is provided an image processing method comprising: an image acquisition step of acquiring a medical image; a segmentation step of performing segmentation on the medical image acquired in the image acquisition step and classifying the medical image into classes indicating features of each local region; a global feature acquisition step of acquiring a global feature indicating an overall feature of the medical image; and a correction step of correcting a class of a correction target region that is a local region whose class is to be corrected in the medical image according to the global feature with reference to a relationship between the global feature and the class.

According to the eleventh aspect, it is possible to obtain the same effect as that in the first aspect.

In the eleventh aspect, the same matters as those specified in the second to tenth aspects can be appropriately combined with each other. In this case, the components that are in charge of the processes or functions specified in the image processing apparatus can be understood as components of the image processing method which are in charge of processes or functions corresponding to the processes or functions.

According to a twelfth aspect, there is provided a program that causes a computer to implement: an image acquisition function of acquiring a medical image; a segmentation function of performing segmentation on the medical image acquired by the image acquisition function and classifying the medical image into classes indicating features of each local region; a global feature acquisition function of acquiring a global feature indicating an overall feature of the medical image; and a correction function of correcting a class of a correction target region that is a local region whose class is to be corrected in the medical image according to the global feature with reference to a relationship between the global feature and the class.

According to the twelfth aspect, it is possible to obtain the same effect as that in the first aspect.

In the twelfth aspect, the same matters as those specified in the second to tenth aspects can be appropriately combined with each other. In this case, the components that are in charge of the processes or functions specified in the image processing apparatus can be understood as components of the program which are in charge of processes or functions corresponding to the processes or functions.

According to the invention, the correction target region is specified according to the global feature with reference to the relationship between the global feature indicating the overall feature of the medical image and the class indicating the local feature of the medical image, and the class of the correction target region class is corrected. Therefore, the correction of the class according to the global feature is automated, and it is possible to reduce the time and effort required to correct the segmentation.

BRIEF DESCRIPTION OF THE DRAWINGS

FIG. 5 is a diagram illustrating an example of a probability map.

FIG. 6 is a diagram schematically illustrating class correction.

FIG. 7 is a diagram illustrating an example of a table indicating a correspondence relationship between a disease name and a lesion.

DESCRIPTION OF THE PREFERRED EMBODIMENTS

Figure 1:
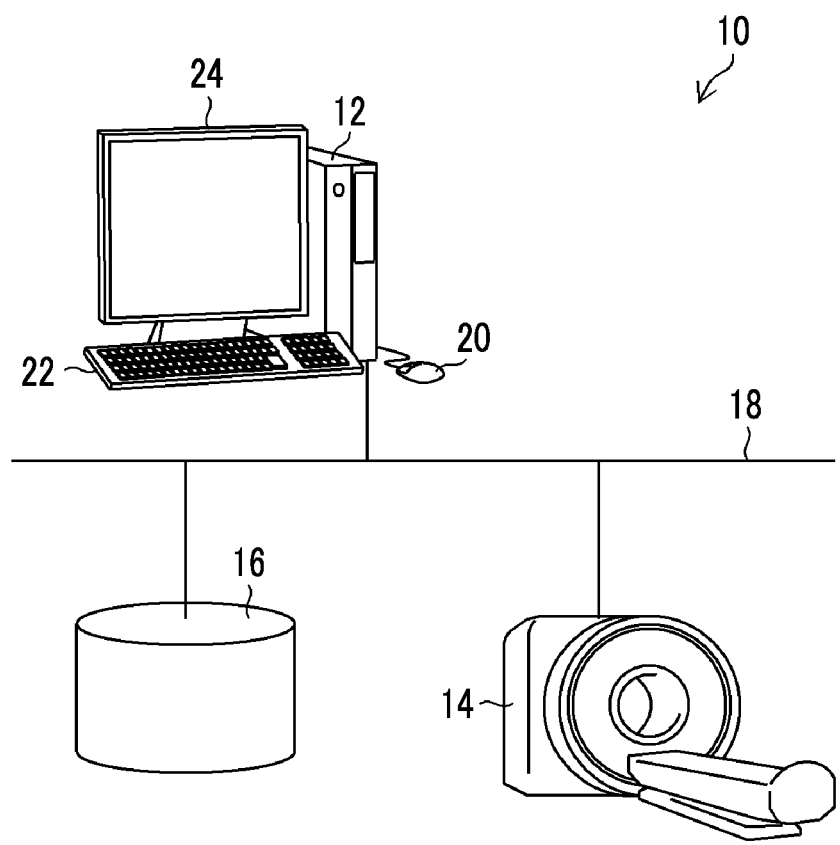
FIG. 1 is a diagram illustrating a schematic configuration of a medical information system according to an embodiment.

Hereinafter, preferred embodiments of the invention will be described in detail with reference to the accompanying drawings. In the specification, the same components are denoted by the same reference numerals and the duplicate description thereof will be appropriately omitted.

[Overall Configuration of Medical Image Processing System]

FIG. 1 is a diagram illustrating a schematic configuration of a medical information system according to an embodiment. A medical information system 10 comprises an image processing apparatus 12, a modality 14, and an image database 16. The image processing apparatus 12, the modality 14, and the image database 16 are connected through a network 18 so as to communicate with each other.

A computer provided in a medical institution can be applied as the image processing apparatus 12. A mouse 20 and a keyboard 22 as an input device are connected to the image processing apparatus 12. In addition, a display device 24 is connected to the image processing apparatus 12.

The modality 14 is an imaging apparatus that captures an image of an examination target part of a subject and generates a medical image. Examples of the modality 14 include an X-ray imaging apparatus, a CT apparatus, an MRI apparatus, a PET apparatus, an ultrasound apparatus, and a CR apparatus using a flat X-ray detector. An endoscopic apparatus may be applied as the modality 14.

In addition, CT is an abbreviation of Computed Tomography. MRI is an abbreviation of Magnetic Resonance Imaging. PET is an abbreviation of Positron Emission Tomography. In some cases, the flat X-ray detector is called a flat panel detector (FPD). CR is an abbreviation of Computed Radiography.

A DICOM standard can be applied as the format of the medical image. Accessory information defined by the DICOM standard may be added to the medical image. In addition, DICOM is an abbreviation of Digital Imaging and Communications in Medicine.

The term "image" in the specification may include the meaning of image data which is a signal indicating an image in addition to the meaning of an image such as a photograph.

A computer comprising a high-capacity storage device can be applied as the image database 16. Software for providing the functions of a database management system is incorporated into the computer. In some cases, the database management system is called a database management system (DBMS).

A local area network (LAN) can be applied as the network 18. In addition, a wide area network (WAN) may be applied as the network 18. The DICOM standard can be applied as the communication protocol of the network 18. In addition, the network 18 may be configured so as to be connected to a public line network or may be configured so as to be connected to a leased line network. The network 18 may be a wired network or a wireless network.

[Image Processing Apparatus]

[Functions of Image Processing Apparatus]

Figure 2:
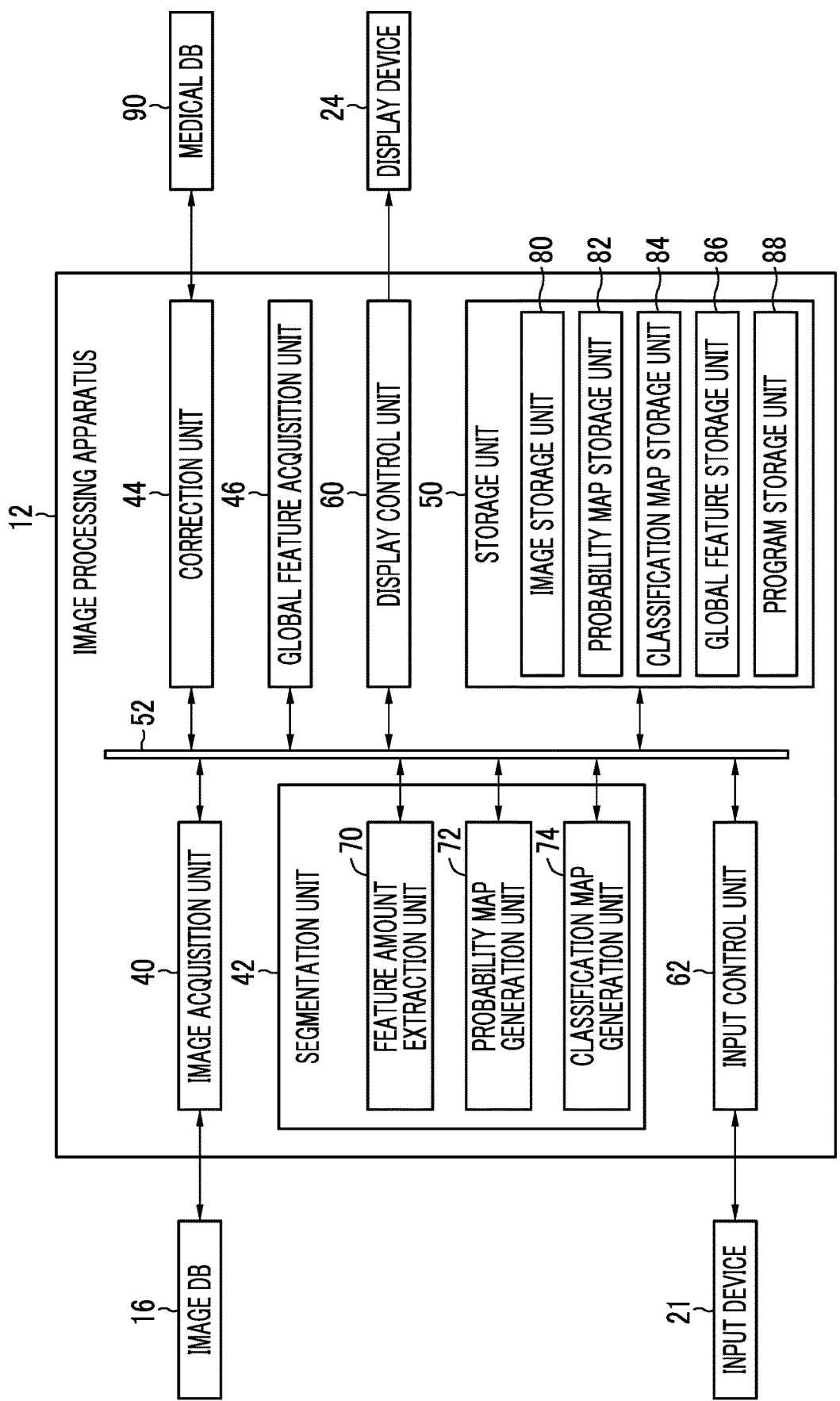
FIG. 2 is a functional block diagram illustrating an image processing apparatus illustrated in FIG. 1.

FIG. 2 is a functional block diagram illustrating the image processing apparatus illustrated in FIG. 1. The image processing apparatus 12 illustrated in FIG. 2 applies, for example, deep learning to efficiently correct a segmentation mask of a medical image. In addition, the correction of the segmentation mask is synonymous with the correction of segmentation. An example of the segmentation of the medical image is the classification of lung tissues into lesions such as bronchiectasis, a honeycomb lung, ground-glass opacity, a reticular lung, and a linear lung.

For example, the segmented medical image is used to calculate the volume of each lesion. A change in the volume of each lesion is an index of the progression of a lung disease such as an interstitial lung disease.

In this embodiment, as the image processing apparatus 12, a discrimination apparatus will be described which automatically classifies whether or not each pixel in a CT image of the lung belongs to a class which is a medically known image pattern in a case in which the CT image of the lung is input. Examples of the medically known image pattern include lesions such as a honeycomb lung, ground-glass opacity, a reticular lung, and a linear lung.

The image processing apparatus 12 comprises an image acquisition unit 40, a segmentation unit 42, a correction unit 44, and a global feature acquisition unit 46. The image processing apparatus 12 comprises a storage unit 50, a display control unit 60, and an input control unit 62.

The image acquisition unit 40, the segmentation unit 42, the correction unit 44, the global feature acquisition unit 46, the storage unit 50, the display control unit 60, and the input control unit 62 are connected through a bus 52 so as to communicate with each other. Hereinafter, each unit of the image processing apparatus 12 will be described in detail.

The image acquisition unit 40 acquires the medical image to be processed. The image processing apparatus 12 stores the acquired medical image in the storage unit 50. FIG. 2 illustrates an aspect in which a medical image is acquired from the image database 16.

The image acquisition unit 40 may acquire a medical image from the modality 14 illustrated in FIG. 1 or may acquire a medical image from a storage device (not illustrated) through the network 18. In addition, the image acquisition unit 40 may acquire a medical image through an information storage medium.

The segmentation unit 42 comprises a feature amount extraction unit 70, a probability map generation unit 72, and a classification map generation unit 74. The segmentation unit 42 performs segmentation on the medical image acquired by the image acquisition unit 40.

That is, the segmentation unit 42 extracts the feature amount of each pixel in the medical image, performs class classification on the basis of the feature amount of each pixel, and generates a classification map. A plurality of consecutive pixels constitute a local region of the medical image. That is, the segmentation unit 42 can perform class classification for each local region of the medical image. Hereinafter, processing for each pixel can be read as processing for each local region.

In this embodiment, a lesion is given as an example of the class. In the specification, the lesion may be called a lesion pattern, a finding, and the like. Further, the segmentation using the segmentation unit 42 will be described in detail below.

The correction unit 44 corrects the segmentation of the medical image with reference to a table indicating the relationship between the global features and the classes stored in a medical database 90. Specifically, in a case in which the class of the local region in the medical image is wrong, the wrong class is corrected on the basis of the relationship between the global features and the classes. The correction of the segmentation of the medical image will be described in detail below.

The global feature acquisition unit 46 acquires the global feature of the medical image used to correct the segmentation of the medical image. Information input by an input device 21 or accessory information of the medical image may be applied as the global feature of the medical image. In addition, for the medical image for which diagnosis has been confirmed, the global feature may be acquired from a system such as an electronic medical record (not illustrated). In this embodiment, a disease name is given as an example of the global feature.

The storage unit 50 stores various types of data in the image processing apparatus 12. The storage unit 50 comprises an image storage unit 80, a probability map storage unit 82, a classification map storage unit 84, a global feature storage unit 86, and a program storage unit 88. A plurality of storage devices or one storage device which is partitioned into a plurality of storage regions may be applied as the storage unit 50. One or more storage devices which are provided outside the image processing apparatus 12 may be applied as the storage unit 50.

The image storage unit 80 stores the medical image acquired by the image acquisition unit 40. The probability map storage unit 82 stores a probability map in which a probability indicating the class likelihood of each pixel is mapped for each local region of the medical image. The probability map is denoted by reference numeral 210 in FIG. 4.

The classification map storage unit 84 stores a classification map generated as the result of segmentation. The classification map is denoted by reference numeral 220 in FIG. 4. The global feature storage unit 86 stores the global feature acquired by the global feature acquisition unit 46. The global feature is denoted by reference numeral 230 in FIG. 6.

The program storage unit 88 stores various programs executed in the image processing apparatus 12. The image processing apparatus 12 executes various programs using the hardware illustrated in FIG. 3 to implement various functions of the image processing apparatus 12.

The display control unit 60 transmits a signal indicating the information to be displayed by a display device 24 to the display device 24. An example of the information to be displayed by the display device 24 is a classification map indicating the segmented medical image.

The input control unit 62 converts a signal indicating input information transmitted from the input device 21 into a signal in a format applied to the image processing apparatus 12. The signal indicating the input information is appropriately transmitted to each unit of the apparatus.

[Hardware Configuration of Image Processing Unit]

<Overall Configuration>

Figure 3:
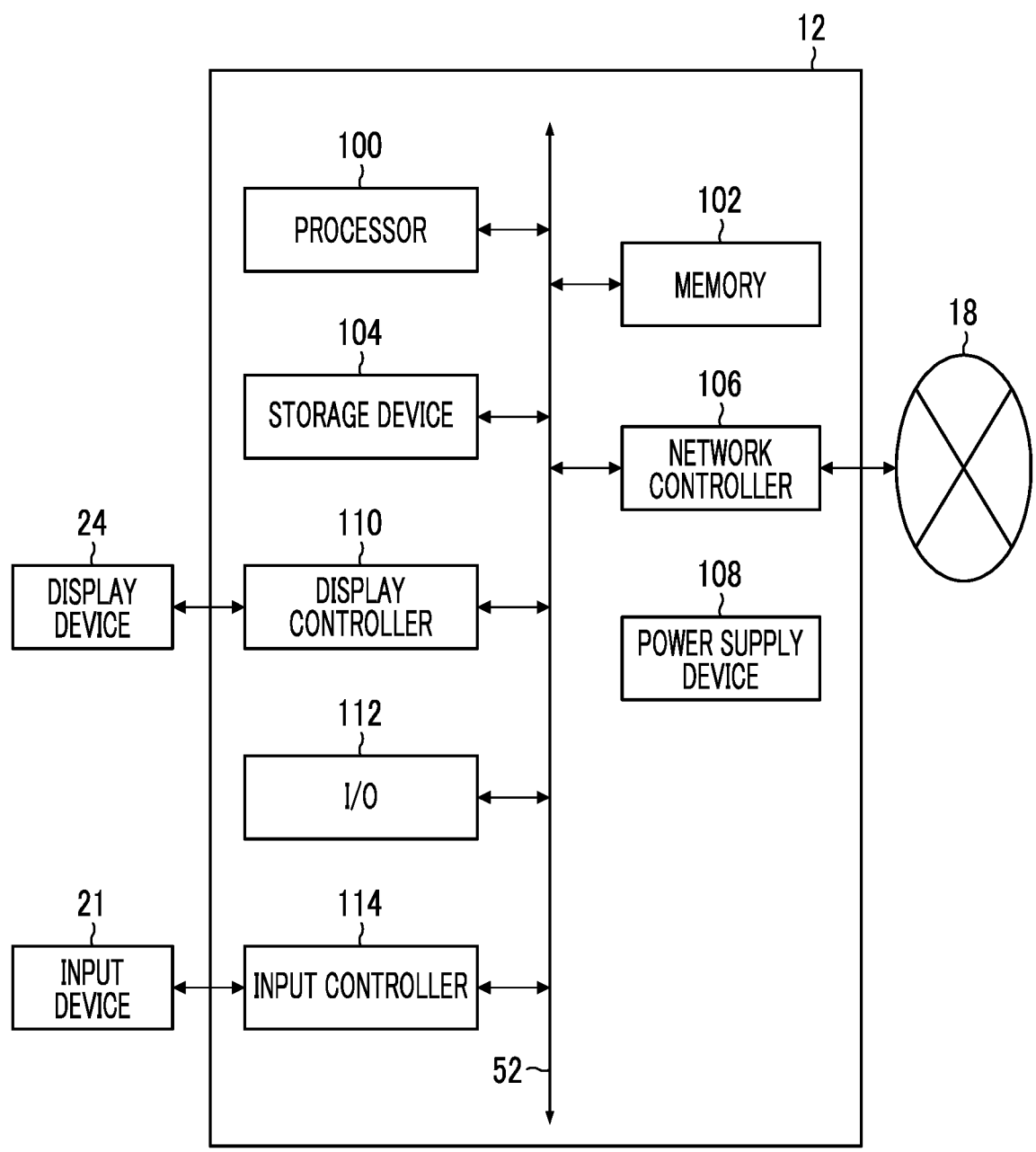
FIG. 3 is a block diagram illustrating a hardware configuration of the image processing apparatus illustrated in FIG. 1.

FIG. 3 is a block diagram illustrating the hardware configuration of the image processing apparatus illustrated in FIG. 1. The image processing apparatus 12 can execute a prescribed program using the hardware illustrated in FIG. 3 to implement various functions.

The image processing apparatus 12 comprises a processor 100, a memory 102, a storage device 104, a network controller 106, and a power supply device 108. Further, the image processing apparatus 12 comprises a display controller 110, an input/output interface 112, and an input controller 114.

The processor 100, the memory 102, the storage device 104, the network controller 106, the display controller 110, the input/output interface 112, and the input controller 114 are connected through the bus 52 so as to perform data communication therebetween.

<Processor>

The processor 100 functions as an overall control unit for the image processing apparatus 12, various arithmetic units, and a storage control unit. The processor 100 executes programs stored in a read only memory (ROM) provided in the memory 102.

The processor 100 may execute a program downloaded from an external storage device through the network controller 106. The external storage device may be connected so as to communicate with the image processing apparatus 12 through the network 18.

The processor 100 performs various processes in cooperation with various programs, using a random access memory (RAM) provided in the memory 102 as an arithmetic region. In this way, various functions of the image processing apparatus 12 are implemented.

The processor 100 controls the reading of data from the storage device 104 and the writing of data to the storage device 104. The processor 100 may acquire various types of data from the external storage device through the network controller 106. The processor 100 can execute various processes, such as calculations, using the acquired various types of data.

The processor 100 may include one device or two or more devices. Examples of the processor 100 include a field programmable gate array (FPGA) and a programmable logic device (PLD). The FPGA and the PLD are devices whose circuit configurations can be changed after manufacture.

Another example of the processor 100 is an application specific integrated circuit (ASIC). The ASIC has a dedicated circuit configuration that is designed in order to perform a specific process.

Two or more devices of the same type can be applied as the processor 100. For example, two or more FPGAs or two PLDs may be used as the processor 100. Two or more devices of different types may be applied as the processor 100. For example, one or more FPGAs and one or more ASICs may be applied as the processor 100.

In a case in which a plurality of processors 100 are provided, the plurality of processors 100 may be configured by one device. As an example in which the plurality of processors 100 are configured by one device, there is an aspect in which a combination of one or more central processing units (CPUs) and software is used to configure one processor and the processor functions as the plurality of processors 100. In addition, the software in the specification is synonymous with a program.

A graphics processing unit (GPU) which is a device specialized for image processing may be applied instead of the CPU or in addition to the CPU. A computer is given as a representative example in which a plurality of processors 100 are configured by one device.

As another example in which the plurality of processors 100 are configured by one device, there is an aspect in which a device that implements all of the functions of a system including the plurality of processors 100 with one IC chip is used. A system on chip (SoC) is given as a representative example of the device that implements all of the functions of the system including the plurality of processors 100 with one IC chip. In addition, IC is an abbreviation of Integrated Circuit.

As such, the hardware structure of the processor 100 is configured by one or more various devices.

<Memory>

The memory 102 comprises a ROM (not illustrated) and a RAM (not illustrated). The ROM stores various programs executed by the image processing apparatus 12. The ROM stores, for example, files and parameters used to execute various programs. The RAM functions as, for example, a temporary data storage region and a work area of the processor 100.

<Storage Device>

The storage device 104 non-temporarily stores various types of data. The storage device 104 may be attached to the outside of the image processing apparatus 12. A high-capacity semiconductor memory device may be applied instead of or in addition to the storage device 104.

<Network Controller>

The network controller 106 controls data communication with an external apparatus. The control of the data communication may include the management of data communication traffic. A known network, such as a local area network (LAN), may be applied as the network 18 connected through the network controller 106.

<Power Supply Device>

A high-capacity power supply device, such as an uninterruptible power supply (UPS), is applied as the power supply device 108. The power supply device 108 supplies power to the image processing apparatus 12 in a case in which a commercial power supply is cut off due to, for example, a power failure.

<Display Controller>

The display controller 110 functions as a display driver that controls the display device 24 on the basis of a command signal transmitted from the processor 100.

<Input/Output Interface>

The input/output interface 112 connects the image processing apparatus 12 and an external apparatus so as to communicate with each other. A communication standard, such as a universal serial bus (USB), may be applied as the input/output interface 112.

<Input Controller>

The input controller 114 converts the format of the signal input by the input device 21 into a format suitable for the processing of the image processing apparatus 12. The information input from the input device 21 through the input controller 114 is transmitted to each unit through the processor 100.

In addition, the hardware configuration of the image processing apparatus 12 illustrated in FIG. 3 is an illustrative example, and some components of the hardware configuration can be appropriately added, removed, and changed.

Detailed Description of Class Classification

Figure 4:
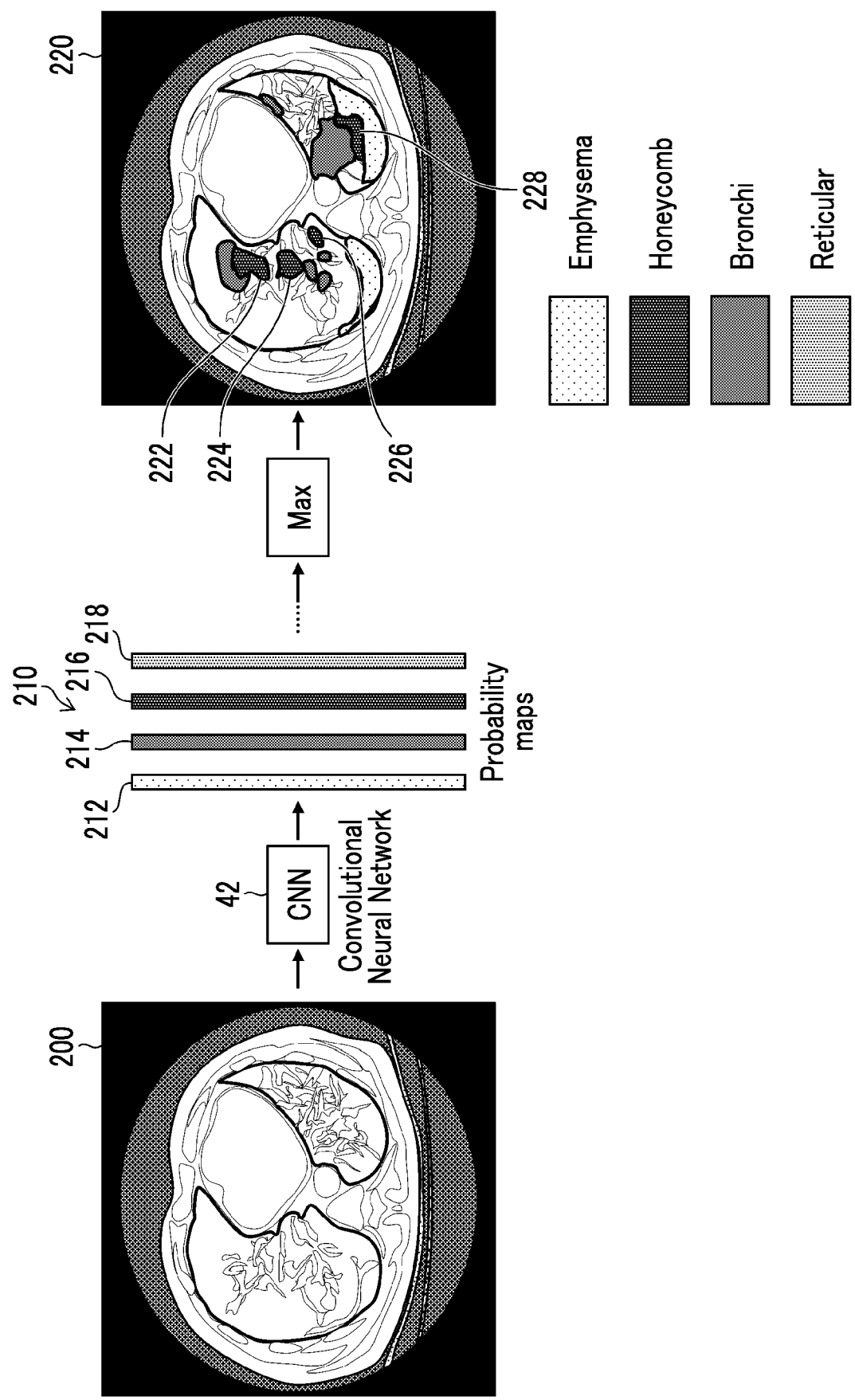
FIG. 4 is a diagram schematically illustrating class classification.

Next, the segmentation of the medical image performed by the segmentation unit 42 illustrated in FIG. 2 will be described. FIG. 4 is a diagram schematically illustrating class classification. As the segmentation of the medical image, the segmentation unit 42 performs multi-class classification which classifies at least some of the pixels constituting a medical image 200 into any one of a plurality of classes.

The segmentation unit 42 generates the probability map 210 from the medical image 200 and applies the probability map 210 to the medical image 200 to generate the classification map 220. A machine learning device, such as a convolutional neural network, is applied as the segmentation unit 42. In addition, CNN illustrated in FIG. 4 is an abbreviation of Convolutional Neural Network.

The segmentation unit 42 calculates a probability indicating the likelihood of a class for each pixel as a score indicating the likelihood of a class and generates the probability map 210. FIG. 4 illustrates an example in which a lesion is applied as the class. In the probability map 210 illustrated in FIG. 4, emphysema is applied as a first class 212, bronchiectasis is applied as a second class 214, a honeycomb lung is applied as a third class 216, and a reticular lung is applied as a fourth class 218. Further, the number of classes may be two or more.

The segmentation unit 42 calculates the probability of each pixel belonging to the first class 212, the probability of each pixel belonging to the second class 214, the probability of each pixel belonging to the third class 216, and the probability of each pixel belonging to the fourth class 218.

FIG. 5 is a diagram illustrating an example of the probability map. FIG. 5 illustrates a table-form probability map 210. FIG. 5 illustrates a local region in which the probability of the third class 216 illustrated in FIG. 4 is the maximum. The probability map 210 illustrated in FIG. 5 includes the probabilities of each class in a first region 222, a second region 224, a third region 226, and a fourth region 228 illustrated in FIG. 4.

As illustrated in FIG. 4, the segmentation unit 42 performs class classification that determines a class having the maximum probability in the probability map 210 as the class of each pixel and generates the classification map 220. In the classification map 220 illustrated in FIG. 4, the first region 222, the second region 224, the third region 226, and the fourth region 228 are classified into the honeycomb lung which is the third class 216.

In this embodiment, the probability indicating the likelihood of a class is given as an example of the score indicating the likelihood of a class. However, the score indicating the likelihood of a class is not limited to the probability as long as it is a value indicating the likelihood of a class.

Detailed Description of Class Correction

Next, the class correction performed by the correction unit 44 illustrated in FIG. 2 will be described in detail. FIG. 6 is a diagram schematically illustrating the class correction. In a case in which there is an error in the class of the classification map 220, it is necessary to correct the class. Relearning can be performed using a corrected classification map 240 in which a class error has been corrected to perform class classification with higher accuracy. That is, the corrected classification map 240 in which the class error has been corrected is very useful data.

FIG. 7 is a diagram illustrating an example of a table indicating the correspondence relationship between disease names and lesions. There is a close relationship between the disease name determined on the basis of the overall feature of the medical image 200 and the lesion determined on the basis of the local feature of the medical image 200. As illustrated in FIG. 7, there are lesions that can exist for each disease name and lesions that are not capable of existing for each disease name.

Therefore, at least one of a table 250 indicating the correspondence relationship between the disease name and the lesion that can exist as illustrated in FIG. 7 or a table (not illustrated) indicating the correspondence relationship between the disease name and the lesion that is not capable of existing is prepared. The table 250 or the table (not illustrated) is stored in the medical database 90 illustrated in FIG. 2. In addition, the disease name may be called an illness name, a disorder name, a diagnosis name, and the like.

Further, RA illustrated in FIG. 7 is an abbreviation for Rheumatoid Arthritis. SSc is an abbreviation of Systemic Sclerosis. PSS is an abbreviation of Progressive Systemic Sclerosis.

OP is an abbreviation of Organizing Pneumonia. COP is an abbreviation of Cryptogenic Organizing Pneumonia.

DIP is an abbreviation of Desquamative Interstitial Pneumoniae. CNPA is an abbreviation of Chronic Necrotizing Pulmonary Aspergillosis. IPF is an abbreviation of Idiopathic Pulmonary Fibrosis. UIP is an abbreviation of Usual Interstitial Pneumonia.

In a case in which the global feature 230 illustrated in FIG. 6 is acquired, the correction unit 44 changes the class that is not capable of originally existing in the classification map 220 and generates the corrected classification map 240. The global feature 230 is input by a doctor who is a user using the input device 21 illustrated in FIG. 2.

In FIG. 6, Not IPF is given as an example of the global feature 230. Not IPF is the global feature 230 indicating that the disease name is not idiopathic pulmonary fibrosis. In addition, the global feature 230 indicating that the disease name is not idiopathic pulmonary fibrosis described in the embodiment is an example of a negative global feature.

The correction unit 44 changes the class that is not capable of originally existing in the disease names other than IPF in the classification map 220 to a class that has the highest probability indicating the likelihood of a class among the classes that can originally exist in the disease names other than IPF. That is, the correction unit 44 extracts a lesion that can exist only in IPF among the classes of the classification map 220 illustrated in FIG. 6 and changes the extracted lesion to a lesion that has the highest probability indicating the likelihood of a lesion among the lesions that can exist in the diseases other than IPF.

Here, for the lesion that can exist only in IPF, a lesion that can exist in the disease name which can be excluded from other conditions may be excluded from the lesions that can exist in the disease names other than IPF. For example, in a case in which a collagen disease lung RA, unclassifiable interstitial pneumonia, and IPS acute exacerbation in the table 250 illustrated in FIG. 7 are excluded and Not IPF is acquired as the global feature 230, the honeycomb lung is changed to another lesion.

In the classification map 220 illustrated in FIG. 6, the first region 222, the second region 224, the third region 226, and the fourth region 228 are classified into the honeycomb lung which is a lesion existing only in IPF. Therefore, the correction unit 44 generates the corrected classification map 240 in which a first region 222A and a fourth region 228A have been changed to the reticular lung, a second region 224A has been changed to emphysema, and a third region 226A has been changed to bronchiectasis.

The correction unit 44 may correct the class of each local region according to a plurality of global features 230. In a case in which the doctor inputs neither summer-type hypersensitivity pneumonitis nor bird-related hypersensitivity pneumonitis as the global feature 230, the class of a region that is classified in a map shape and exists only in summer-type hypersensitivity pneumonitis and bird-related hypersensitivity pneumonitis is changed to a class having the highest probability among the classes with shapes other than the map shape.

That is, the correction unit 44 can correct the class of each local region according to the logical product of the plurality of global features 230. The correction unit 44 may correct the class of each local region according to the logical sum of the plurality of global features 230. In this aspect, the table 250 illustrated in FIG. 7 may store the relationship among the logical product of the plurality of global features 230, the logical sum of the plurality of global features 230, and lesions.

IPF indicating idiopathic pulmonary fibrosis may be acquired as the global feature 230. In addition, the global feature 230 indicating idiopathic pulmonary fibrosis is an example of a positive global feature.

In a case in which IPF is acquired as the global feature 230, the correction unit 44 changes the class that is not capable of originally existing in IPF in the classification map 220 to a class that has the highest probability among the classes that can originally exist in IPF.

As another example of the positive global feature, an example in which the collagen disease lung illustrated in FIG. 7 is acquired as the global feature 230 will be described. The doctor who sees the classification map 220 illustrated in FIG. 4 inputs the collagen disease lung SSc as the global feature 230. The correction unit 44 changes the class of the region classified into the class other than bronchiectasis, traction bronchiectasis, and ground-glass opacity to a class having the highest probability among bronchiectasis, traction bronchiectasis, and ground-glass opacity.

In addition, even in a case in which the positive global feature is applied, the class of each local region may be corrected according to the logical product of the plurality of global features 230 and the logical sum of the plurality of global features 230.

[Procedure of Image Processing Method]
[Flowchart of Entire Image Processing Method]

Figure 8:
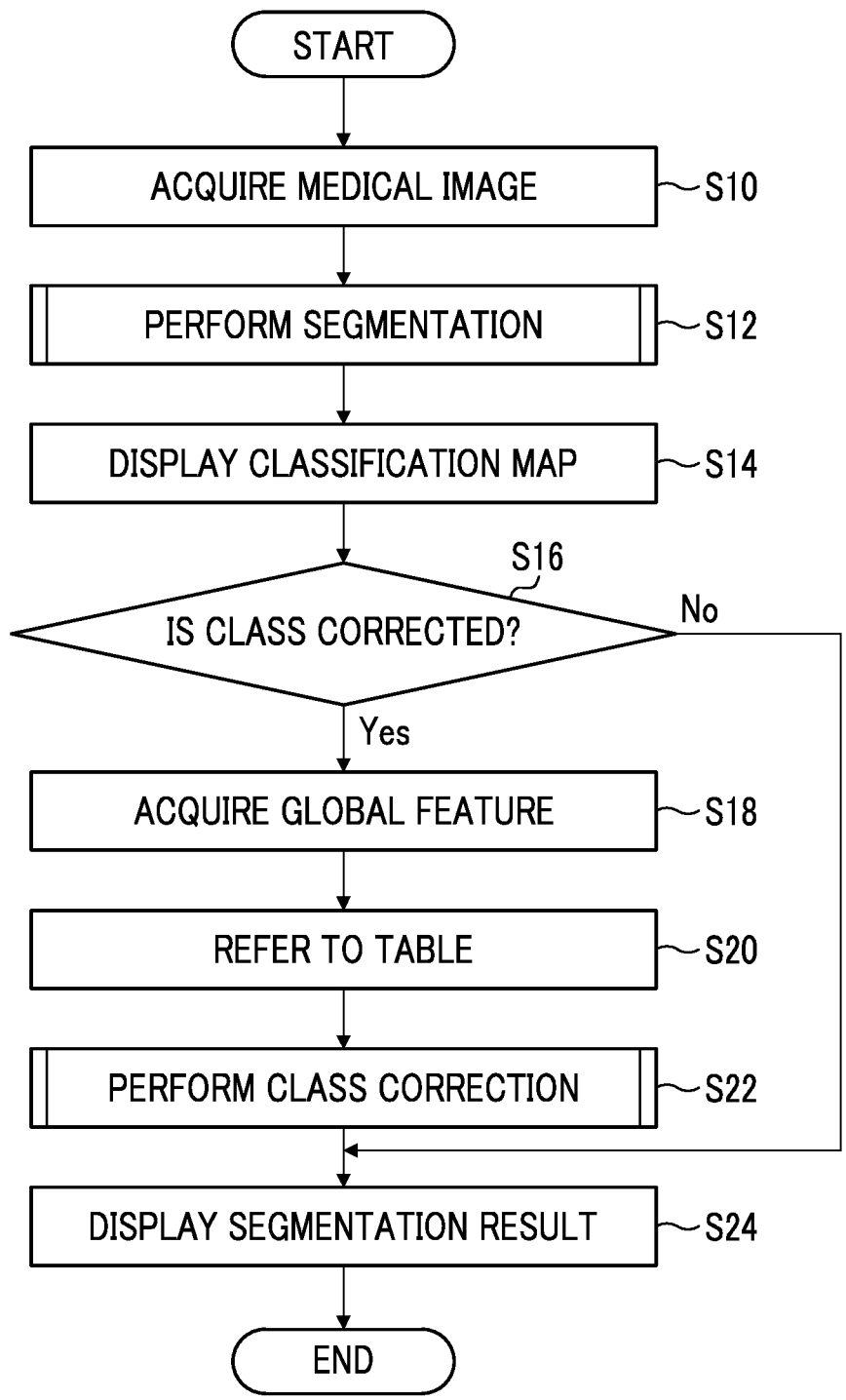
FIG. 8 is a flowchart illustrating the procedure of an image processing method.

Next, the procedure of an image processing method applied to the image processing apparatus 12 illustrated in FIG. 2 will be described. FIG. 8 is a flowchart illustrating the procedure of the image processing method. The image processing apparatus 12 executes a program to implement functions corresponding to each step illustrated in FIG. 8.

In a medical image acquisition step S10, the image acquisition unit 40 illustrated in FIG. 2 acquires a medical image from, for example, the image database 16. The image acquisition unit 40 stores the medical image to the image storage unit 80. After the medical image acquisition step S10, the process proceeds to a segmentation step S12.

In the segmentation step S12, the segmentation unit 42 performs segmentation on the medical image and generates the classification map 220 illustrated in FIG. 4. The segmentation unit 42 stores the classification map 220 in the probability map storage unit 82. After the segmentation step S12, the process proceeds to a classification map display step S14.

In the classification map display step S14, the display control unit 60 transmits a display signal indicating the classification map 220 illustrated in FIG. 4 to the display device 24. The display device 24 displays the classification map 220. After the classification map display step S14, the process proceeds to a class correction determination step S16.

In the class correction determination step S16, the correction unit 44 determines whether or not an instruction to correct the class in the classification map 220 has been acquired. In a case in which the correction unit 44 has not acquired the instruction to correct the class in the classification map 220, the determination result is "No", and the process proceeds to a segmentation result display step S24.

On the other hand, in a case in which the correction unit 44 has acquired the instruction to correct the class in the classification map 220 in the class correction determination step S16, the determination result is "Yes", and the process proceeds to a global feature acquisition step S18. That is, in the class correction determination step S16, the image processing apparatus waits for an input indicating the correction of the classification map 220 from the doctor who sees the classification map 220 displayed on the display device 24.

In the class correction determination step S16, the display control unit 60 may direct the display device 24 to display a screen asking whether or not the classification map 220 needs to be corrected.

In the global feature acquisition step S18, the global feature acquisition unit 46 acquires the global feature 230 input from the input device 21 through the input control unit 62. The global feature acquisition unit 46 stores the global feature 230 in the global feature storage unit 86. After the global feature acquisition step S18, the process proceeds to a table reference step S20.

In the table reference step S20, the correction unit 44 specifies a correction target region with reference to the table 250 stored in the medical database 90. The correction target region includes the comprehensive concept of a correction target pixel and a correction target local region. After the table reference step S20, the process proceeds to a class correction step S22.

In the class correction step S22, the correction unit 44 corrects the classification map 220 to generate the corrected classification map 240. The correction unit 44 stores the corrected classification map 240 in the classification map storage unit 84. After the class correction step S22, the process proceeds to a segmentation result display step S24.

In the segmentation result display step S24, the display control unit 60 transmits a display signal indicating the classification map 220 that does not need to be corrected or the corrected classification map 240 to the display device 24. The display device 24 displays the classification map 220 that does not need to be corrected or the corrected classification map 240. After the segmentation result display step S24, the image processing apparatus 12 ends the procedure of the image processing method.

[Procedure of Segmentation Step]

Figure 9:
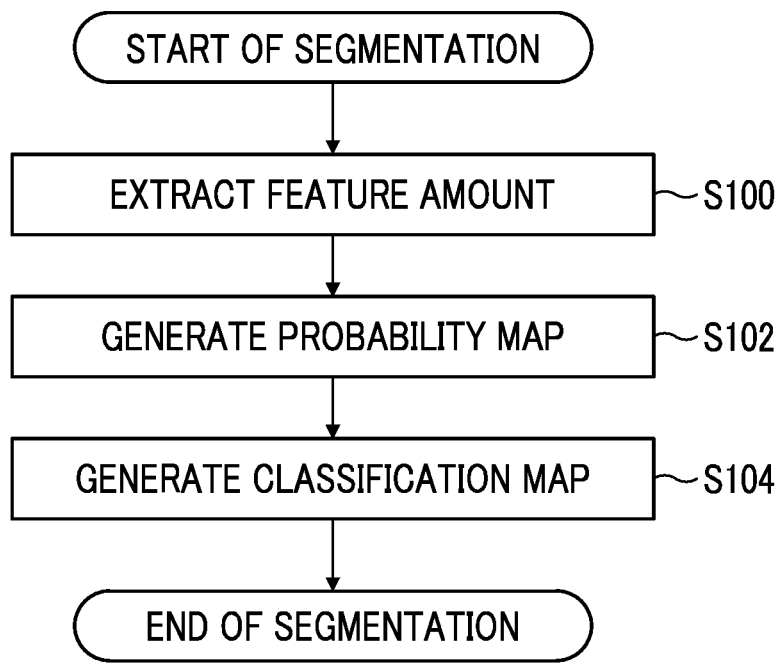
FIG. 9 is a flowchart illustrating the procedure of a segmentation step illustrated in FIG. 8.

FIG. 9 is a flowchart illustrating the procedure of the segmentation step illustrated in FIG. 8. In a feature amount extraction step S100, the feature amount extraction unit 70 extracts the feature amount of each pixel of the medical image 200. After the feature amount extraction step S100, the process proceeds to a probability map generation step S102.

In the probability map generation step S102, the probability map generation unit 72 generates the probability map 210. The probability map generation unit 72 stores the probability map 210 in the probability map storage unit 82. After the probability map generation step S102, the process proceeds to a classification map generation step S104. In addition, the probability map generation unit 72 according to the embodiment is an example of a score calculation unit.

In the classification map generation step S104, the classification map generation unit 74 generates the classification map 220. The classification map generation unit 74 stores the classification map 220 in the classification map storage unit 84. After the classification map generation step S104, the image processing apparatus 12 ends the segmentation step S12 and performs the classification map display step S14.

[Procedure of Class Correction Step]

Figure 10:
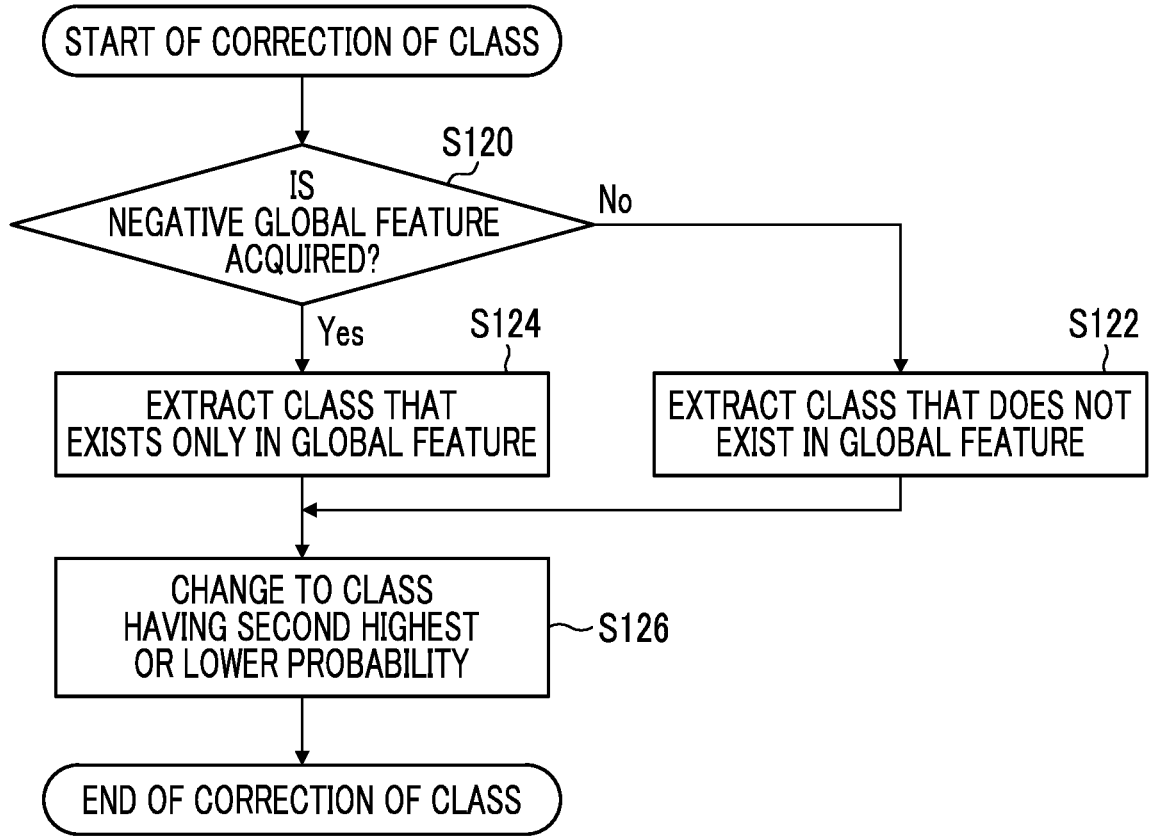
FIG. 10 is a flowchart illustrating the procedure of a class correction step illustrated in FIG. 8.

FIG. 10 is a flowchart illustrating the procedure of the class correction step illustrated in FIG. 8. In a global feature determination step S120, the correction unit 44 determines whether the acquired global feature 230 is a negative global feature or a positive global feature.

In the case of the positive global feature, the determination result is "No", and the process proceeds to a positive information class extraction step S122. On the other hand, in the case of the negative global feature, the determination result is "Yes", and the process proceeds to a negative information class extraction step S124.

In the positive information class extraction step S122, the correction unit 44 extracts a class that is not capable of originally existing in the global feature 230 from the classification map 220 with reference to the table 250.

For example, in a case in which the global feature 230 is IPF, the correction unit 44 extracts a class that is not capable of originally existing in IPF from the classification map 220. After the positive information class extraction step S122, the process proceeds to a class change step S126. In addition, the class that is not capable of originally existing in the global feature 230 in the embodiment is an example of a class that does not correspond to the global feature.

In the negative information class extraction step S124, the correction unit 44 extracts a class that originally exists only in the global feature 230. For example, as described with reference to FIGS. 5 to 8, in a case in which the global feature 230 is Not IPF, the honeycomb lung is extracted from the classification map 220. After the negative information class extraction step S124, the process proceeds to the class change step S126.

In the class change step S126, the correction unit 44 changes the class of the correction target region to a class having the highest probability indicating the likelihood of a class among the classes that can exist in the global feature 230. After the class change step S126, the image processing apparatus 12 ends the class correction step S22 and performs the segmentation result display step S24.

[Description of Example of Machine Learning]

Figure 11:
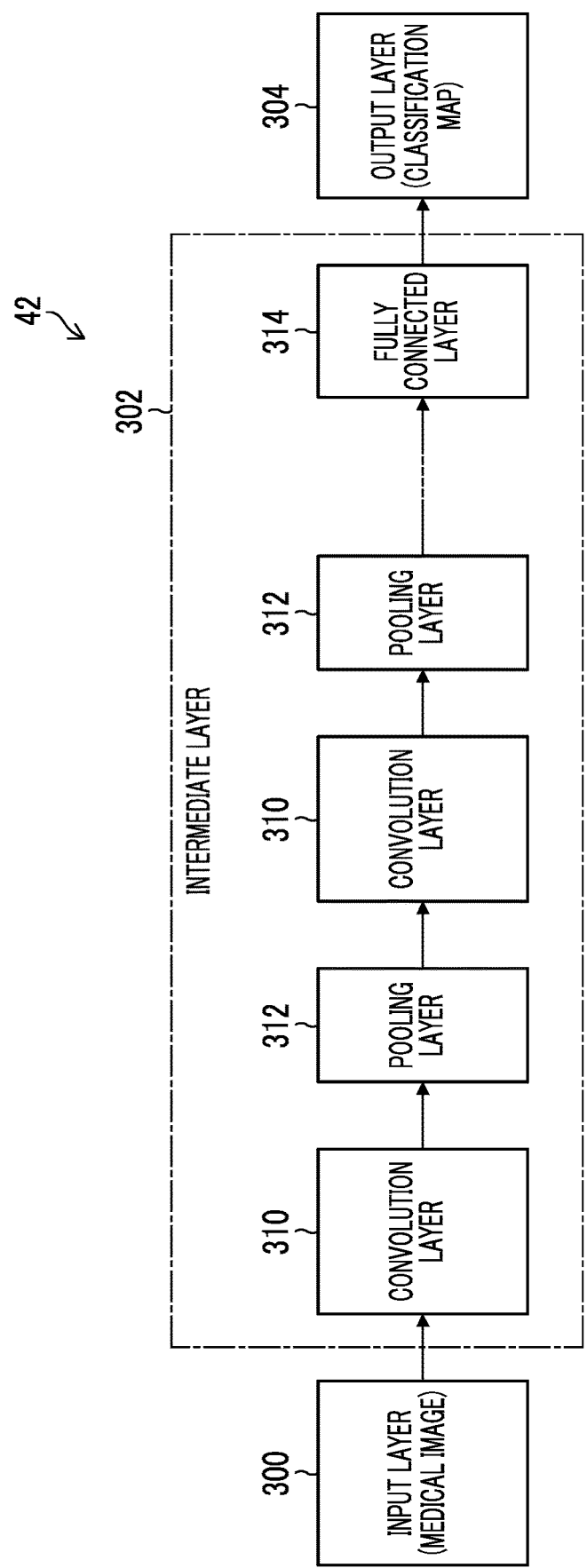
FIG. 11 is a block diagram illustrating a segmentation unit to which a convolutional neural network is applied.

An example of the machine learning applied to the segmentation unit 42 illustrated in FIG. 2 will be described. FIG. 11 is a block diagram illustrating the segmentation unit to which a convolutional neural network is applied.

The segmentation unit 42, to which the convolutional neural network is applied, illustrated in FIG. 11 comprises an input layer 300, an interlayer 302, and an output layer 304. The interlayer 302 comprises a plurality of sets of a convolution layer 310 and a pooling layer 312, and a fully connected layer 314. Each layer has a structure in which a plurality of nodes are connected using edges.

The medical image 200 illustrated in FIG. 4 is input to the input layer 300. The interlayer 302 extracts features from the medical image 200 input by the input layer 300. The convolution layer 310 performs a filtering process on nearby nodes in the previous layer to acquire a feature map. The convolution layer 310 performs a convolution operation using a filter as the filtering process.

The pooling layer 312 reduces the feature map output from the convolution layer 310 to generate a new feature map. The convolution layer 310 performs feature extraction, such as edge extraction, from the medical image 200. The pooling layer 312 imparts robustness such that the extracted feature is not affected by, for example, parallel translation.

The interlayer 302 may adopt an aspect in which the convolution layers 310 are continuous and an aspect in which a normalization layer is provided. In addition, the weights and biases of the filters used in each convolution layer 310 are automatically learned in advance using a large amount of learning data.

The segmentation unit 42 using the convolutional neural network, uses a pair of the medical image 200 and the classification map 220 as learning data and performs learning using a large number of correct answer pairs, such as about several thousands of pairs to several tens of thousands of pairs, to generate a classification map.

Further, the segmentation unit 42 using the convolutional neural network uses a pair of the medical image 200 and the corrected classification map 240 as learning data for relearning and can perform learning using the learning data for relearning to generate the classification map 220 with high accuracy. In addition, the corrected classification map 240 described in the embodiment is an example of the correction result of the class.

The image processing apparatus 12 comprising the segmentation unit 42 using the convolutional neural network may be applied to generation learning data. For example, in a case in which a large number of medical images 200 are used to generate learning data, it is necessary to verify the validity of the classification map 220 generated from the medical images 200.

It takes a lot of time and effort for the doctor to manually correct the classification map 220. Therefore, machine learning is auxiliarily performed to generate the classification map 220 from the medical image 200. The doctor inputs the classification map 220 and the global feature 230 to the image processing apparatus 12. The image processing apparatus 12 can correct the classification map 220 to generate the corrected classification map 240.

In addition, the configuration of the segmentation unit 42 to which the convolutional neural network illustrated in FIG. 11 is applied is an illustrative example, and components can be appropriately added, deleted, and modified.

[Application Examples to Program]

The image processing apparatus 12 and the image processing method described above can be configured as a program that causes a computer to implement functions corresponding to each unit of the image processing apparatus 12 or functions corresponding to each step of the image processing method.

Examples of the functions corresponding to each step or the like include a medical image acquisition function, a segmentation function, a classification mask correction function, and a global feature acquisition function. In addition, examples of the functions corresponding to each step or the like include a probability map generation function, a probability map storage function, a classification map storage function, a global feature storage function, a corrected classification map storage function, and a display signal transmission function.

The medical image acquisition function corresponds to the image acquisition unit 40 illustrated in FIG. 2. The segmentation function corresponds to the segmentation unit 42. The classification mask correction function corresponds to the correction unit 44. The global feature acquisition function corresponds to the global feature acquisition unit 46. The probability map generation function corresponds to the probability map generation unit 72.

The probability map storage function corresponds to the storage of the probability map 210 in the probability map storage unit 82. The classification map storage function corresponds to the storage of the classification map 220 in the classification map storage unit 84. The global feature storage function corresponds to the storage of the global feature 230 in the global feature storage unit 86.

The corrected classification map storage function corresponds to the storage of the corrected classification map 240 in the classification map storage unit 84. The display signal transmission function corresponds to the transmission of the display signal indicating the classification map 220 to the display device 24 by the display control unit 60 and the transmission of the display signal indicating the corrected classification map 240 to the display device 24 by the display control unit 60.

The program causing the computer to implement the above-mentioned information processing functions can be stored in a computer readable information storage medium which is a non-transitory tangible information storage medium and can be provided through the information storage medium. In addition, instead of the aspect in which the program is stored in the non-transitory information storage medium and is then provided, a program signal may be provided through the network.

[Operation and Effect]

According to the image processing apparatus and the image processing method having the above-mentioned configuration, it is possible to obtain the following operation and effect.

[1]

The classification map 220 indicating the class classification of the medical image 200 is corrected according to the global feature 230 with reference to the table 250 indicating the relationship between the global feature 230, such as a disease name, indicating the overall feature of the medical image 200 and the class, such as a lesion, based on the local feature of the medical image 200. Therefore, the correction of the classification map 220 according to the global feature 230 is automated, and it is possible to reduce the time and effort required to correct the classification map 220.

For example, in a case in which the doctor who is a user is aware of an error in the classification map 220 at the time of making a report, the doctor can input the global feature 230 and automatically generate the corrected classification map 240 from the classification map 220. This makes it possible for the doctor to effectively make a report.

[2]

The class having the highest score which indicates the likelihood of a class for each local region is adopted as the class of each local region. This makes it possible to perform class classification with high accuracy.

[3]

The class of the correction target region is corrected to a class having the highest score among the classes corresponding to the global feature 230. This makes it possible to correct the class with high accuracy.

[4]

The probability indicating the likelihood of a class is applied as the score indicating the likelihood of a class. This makes it possible to correct the class using the probability indicating the likelihood of a class.

[5]

The negative global feature or the positive global feature can be applied as the global feature 230. This makes it possible to correct the class according to various correspondence relationships between the global feature 230 and the class.

[6]

The relearning of the segmentation unit 42 to which the convolutional neural network is applied is performed using the medical image 200 and the corrected classification map 240 as learning data. This makes it possible to perform segmentation with higher accuracy.

Modification Examples

Modification Examples of Class Correction

Among the pixels around the correction target pixel, there may be a pixel that is classified into the class into which the correction target pixel is to be originally classified. Therefore, the class of a pixel that is at the minimum distance from the correction target pixel and is classified into a class different from the class of the correction target pixel can be applied as the class of the correction target pixel. In addition, the modification example of the class correction can be applied to a local region composed of a plurality of consecutive pixels.

According to this modification example, it is possible to achieve at least one of shortening the period of the class correction process or reducing the processing load

[Modification Examples of Medical Image]

In this embodiment, the CT image of the lung is given as an example of the medical image. However, the medical images of organs other than the lung may be used. Further, the medical image is not limited to a two-dimensional image. The medical image may be a three-dimensional image. In the case of the three-dimensional image, class classification is performed for each voxel, and class correction is performed for each voxel.

[Modification Examples of Global feature]

In this embodiment, the disease name is given as an example of the global feature 230. However, the global feature 230 may be information that is related to the target medical image and indicates a feature related to the class of a local region, such as a voxel, or information indicating a feature that affects class classification.

For example, the global feature 230 may be information based on the class of one or more voxels or one or more local regions at a position different from the position of the voxel or the local region classified into a certain class. The global feature 230 can be applied to correct a global feature 230 of a voxel or a local region that is close to a target voxel or a target local region.

Further, the global feature 230 may be information related to a subject of the target medical image. The information related to the subject may be acquired from the analysis result of the target medical image, may be information manually input by the doctor, or the information related to the subject may be acquired from another system connected to the image processing apparatus 12. For example, an electronic medical record system is given as an example of another system.

Specific examples of the global feature 230 include a disease name, a physique, age, sex, a previous illness, and an imaging state. The physique, the age, the sex, and the previous illness are examples of information related to the subject. Examples of the physique include height and weight. Examples of the imaging state include the state of expiration and the state of inspiration in a case in which the image of the lung is captured.

[Modification Examples of Class]

In this embodiment, the lesion is given as an example of the class. However, for example, the features of the image patterns of inflammation, tumor, non-tumor, and the like may be applied as the class. In addition, in a case in which there is a standard classification for each modality that generates medical images, the standard classification for each modality can be applied to the class.

For Combinations of Embodiment, Modification Examples, and the Like

The components described in the above-mentioned embodiment and the components described in the application examples can be appropriately combined with each other. In addition, some of the components may be replaced. In the above-described embodiment of the invention, components can be appropriately changed, added, and removed without departing from the scope and spirit of the invention. The invention is not limited to the above-described embodiment and can be changed and modified in various ways by those skilled in the art without departing from the technical idea of the invention.

EXPLANATION OF REFERENCES

10: medical information system
12: image processing apparatus
14: modality
16: image database
18: network
20: mouse
21: input device
22: keyboard
24: display device
40: image acquisition unit
42: segmentation unit
44: correction unit
46: global Feature acquisition unit
50: storage unit
52: bus
60: display control unit
62: input control unit
70: feature amount extraction unit
72: probability map generation unit
74: classification map generation unit
80: image storage unit
82: probability map storage unit
84: classification map storage unit
86: global feature storage unit
88: program storage unit
90: medical database
100: processor
102: memory
104: storage device
106: network controller
108: power supply device
110: display controller
112: input/output Interface
114: input controller
200: medical image
210: probability map
212: first class
214: second class
216: third class
218: fourth class
220: classification map
222: first region
222A: first region
224: second region
224A: second region
226: third region
226A: third region
228: fourth region
228A: fourth region
240: corrected classification map
250: table
300: input layer
302: interlayer
304: output layer
310: convolution layer
312: pooling layer
314: fully connected layer
S10 to S24: each step of image processing method
S100 to S104: each step of segmentation step
S120 to S126: each step of class correction step

What is claimed is:

1. An image processing apparatus comprising at least one processor configured to:
acquire a medical image;
perform segmentation on the medical image and classifies the medical image into classes indicating features of each local region;
calculate a score indicating a likelihood of each of a plurality of classes corresponding to a global feature indicating an overall feature of the medical image for each local region;
apply a class having a highest score as the class of each local region;
acquire the global feature; and
correct a class of a correction target region that is a local region whose class is to be corrected in the medical image according to the global feature with reference to a table representing a correspondence relationship between the global feature and the class;
wherein the at least one processor applies the class having the highest score among the classes corresponding to the global feature as the class of the correction target region in a case in which the class of the correction target region is corrected.

2. The image processing apparatus according to claim 1, wherein the at least one processor calculates a probability indicating the likelihood of a class as the score.

3. The image processing apparatus according to claim 1, wherein the at least one processor corrects the class of the correction target region to a class of a local region which is at a minimum distance from the correction target region, the class of the local region being different from the class of the correction target region.

4. The image processing apparatus according to claim 1, wherein, in a case in which a negative global feature is acquired, the at least one processor sets, as the correction target region, a local region in a class corresponding only to the global feature.

5. The image processing apparatus according to claim 1, wherein, in a case in which a positive global feature is acquired, the at least one processor sets, as the correction target region, a local region in a class that does not correspond to the global feature.

6. The image processing apparatus according to claim 1, wherein the at least one processor corrects the class of the correction target region according to a plurality of the global features.

7. The image processing apparatus according to claim 1, wherein the at least one processor refers to the table in which the relationship between the global feature and the class is stored.

8. The image processing apparatus according to claim 1, further comprising a machine Learner configured to perform relearning using a set of a medical image in which a segmentation result has been corrected and a correction result of the class as learning data.

9. An image processing method comprising:
acquiring a medical image;
performing segmentation on the medical image and classifying the medical image into classes indicating features of each local region;
calculating a score indicating a likelihood of each of a plurality of classes corresponding to a global feature indicating an overall feature of the medical image for each local region;
applying a class having a highest score as the class of each local region;
acquiring the global feature;
correcting the class of a correction target region that is a local region whose class is to be corrected in the medical image according to the global feature with reference to a table representing a correspondence relationship between the global feature and the class; and
applying the class having the highest score among the classes corresponding to the global feature as the class of the correction target region in a case in which the class of the correction target region is corrected.

10. A non-transitory computer readable storage medium storing commands that are read by a computer and cause the computer to implement:
an image acquisition function of acquiring a medical image;
a segmentation function of performing segmentation on the medical image acquired by the image acquisition function and classifying the medical image into classes indicating features of each local region;
a global feature acquisition function of acquiring a global feature indicating an overall feature of the medical image; and
a correction function of correcting the class of a correction target region that is a local region whose class is to be corrected in the medical image according to the global feature with reference to a table representing a correspondence relationship between the global feature and the class,
wherein the segmentation function calculates a score indicating a likelihood of each of a plurality of classes corresponding to the global feature for each local region, and applies a class having a highest score as the class of each local region,
wherein the correction function applies the class having the highest score among the classes corresponding to the global feature as the class of the correction target region in a case in which the class of the correction target region is corrected.

* * * * *